(12) United States Patent  
Koledin

(10) Patent No.: US 8,783,251 B2  
(45) Date of Patent: Jul. 22, 2014

(54) ENHANCED MANUALLY ACTUATED PRESSURE CONTROLLED MODULATOR TECHNOLOGY

(75) Inventor: Michael Koledin, Charlotte, NC (US)

(73) Assignee: Piper Medical, Inc, Carmichael, CA (US)

( * ) Notice: Subject to any disclaimer, the term of this patent is extended or adjusted under 35 U.S.C. 154(b) by 855 days.

(21) Appl. No.: 12/930,896

(22) Filed: Jan. 19, 2011

(65) Prior Publication Data

US 2011/0197892 A1 Aug. 18, 2011

Related U.S. Application Data

(60) Provisional application No. 61/337,989, filed on Feb. 12, 2010.

(51) Int. Cl.
*A61M 11/00* (2006.01)

(52) U.S. Cl.
USPC ................................. 128/205.24; 128/204.18

(58) Field of Classification Search
CPC .............. A61M 16/20; A61M 16/208; A61M 2016/0039; A61M 11/06; A61M 16/01; A62B 9/02
USPC ........................... 128/205.24, 204.18, 204.23
See application file for complete search history.

(56) References Cited

U.S. PATENT DOCUMENTS

| | | |
|---|---|---|
| 2,774,346 A | 12/1956 | Halliburton |
| 3,068,856 A | 12/1962 | Bird |
| 3,191,596 A | 6/1965 | Bird |
| 3,653,379 A | 4/1972 | Glenn |
| 3,753,436 A | 8/1973 | Bird |
| 3,916,888 A | 11/1975 | Buck |
| 3,916,890 A | 11/1975 | Freeman |
| 3,918,447 A | 11/1975 | Inkster |
| 3,974,828 A | 8/1976 | Bird |
| 3,976,065 A | 8/1976 | Durkan |
| 4,022,202 A | 5/1977 | Price |
| 4,039,139 A | 8/1977 | Bird |
| 4,197,843 A | 4/1980 | Bird |
| 4,429,688 A | 2/1984 | Duffy |
| 4,436,090 A | 3/1984 | Darling |
| 4,502,481 A | 3/1985 | Christian |
| 4,592,349 A | 6/1986 | Bird |
| 4,646,733 A | 3/1987 | Stroh |
| 4,823,828 A | 4/1989 | McGinnis |
| 5,007,420 A | 4/1991 | Bird |
| 5,014,694 A | 5/1991 | DeVries |
| 5,116,088 A | 5/1992 | Bird |
| 5,127,400 A | 7/1992 | DeVries |
| 5,165,398 A | 11/1992 | Bird |
| 5,199,426 A | 4/1993 | Aldworth |

(Continued)

*Primary Examiner* — Steven Douglas

(57) ABSTRACT

A dual area pressure pulmonary modulator apparatus which provides constant flow, pressure cycled ventilatory support to patients that is additionally equipped with fluid conduits in the valve mechanism and body that allow the clinician or user to manually actuate inhalation by occluding a fluid path emanating from the modulator. Such feature is useful for when the device stops cycling due to physiological changes of the patient, for determining if the patient is cycling the device or if the device is automatically cycling by nature of its setting, coordinating medical procedures with the breathing of the patient, increasing the PEEP beyond the intrinsic design PEEP of the device for a given PIP setting, increasing inspiratory hold time, and providing an easy to use alternative mode of operation for users with less sophistication.

13 Claims, 8 Drawing Sheets

(56) References Cited

U.S. PATENT DOCUMENTS

| | | |
|---|---|---|
| 5,230,330 A | 7/1993 | Price |
| 5,275,153 A | 1/1994 | Kay |
| 5,307,794 A | 5/1994 | Rauterkus |
| 5,400,779 A | 3/1995 | De Resende |
| 5,423,313 A | 6/1995 | Olsson |
| 5,425,535 A | 6/1995 | Gee |
| 5,443,062 A | 8/1995 | Hayes |
| 5,460,175 A | 10/1995 | Foote |
| 5,537,999 A * | 7/1996 | Dearman et al. ......... 128/205.25 |
| 5,555,880 A | 9/1996 | Winter |
| 5,564,416 A | 10/1996 | Jones |
| 5,572,993 A | 11/1996 | Kurome |
| 6,067,984 A | 5/2000 | Piper |
| 2003/0000529 A1* | 1/2003 | Kay .......................... 128/204.26 |
| 2010/0199991 A1* | 8/2010 | Koledin .................. 128/205.12 |

* cited by examiner

ENHANCED MANUALLY ACTUATED PRESSURE CONTROLLED MODULATOR TECHNOLOGY

CROSS-REFERENCE TO RELATED PATENTS

This application claims the benefit under 35 U.S.C. 119(e) of U.S. provisional application Ser. No. 61/337,989 filed Feb. 12, 2010, which is incorporated by reference herein in its entirety.

STATEMENT REGARDING FEDERALLY SPONSORED RESEARCH

Not Applicable

BACKGROUND OF THE INVENTION

1. Field of the Invention

This invention pertains generally to respiratory ventilation devices with a constant flow pulmonary modulator and equipped with a manually actuating feature, and more specifically to respiratory ventilation devices with a constant flow pulmonary modulator, as described in U.S. Pat. No. 6,067,984, equipped with a feature to allow the clinician or user to easily manually activate inhalation, thus allowing a user to: 1. cycle the device and initiate inhalation immediately in the event that the device stops providing ventilatory supports and "stalls"; 2. detect if the device is automatically cycling or if the patient is triggering the device; 3. synchronize ventilation with other medical procedures; 4. increase Positive End Expiratory Pressure (PEEP) beyond the intrinsic design value for a given Peak Inspiratory Pressure (PIP) setting; and/or 5. provide an inspiratory hold when desired.

2. Description of the Background Art

A fundamental aspect of providing respiratory care to a patient is the ability to provide ventilatory support to patients requiring respiratory assistance. Ventilatory support is typically provided by clinicians through the use of a manual resuscitator or an automatic ventilatory device.

Manual resuscitators are typically equipped with a self-inflating bag, a set of check valves which control the direction of inhalation and exhalation gases, and a patient interface which is usually either a face mask or a port for connection to and endotracheal tube. Manual resuscitators are usually supplied with a continuous flow of gas containing a known percentage of oxygen. The operator of a manual resuscitator inflates the patient with oxygen enriched air by squeezing the self-inflating bag thus applying pressure and causing gas to flowing into the patient's lungs. Inhalation ends and exhalation begins when the operator stops squeezing the bag, allowing the pressurized gas in the patient's lungs to escape to the ambient environment. Most manual resuscitators are equipped with the means to maintain a small minimum positive pressure on the patient's lungs throughout exhalation commonly called Positive End Expiratory Pressure (PEEP). During exhalation, the self-inflating bag re-inflates and process may be repeated. Manual resuscitators are simple, inexpensive, and are easy to coordinate ventilation with other medical procedures. Unfortunately, manual resuscitators are easy to misuse. A large number of studies have been published which show that irregardless whether the operator of the manual resuscitator is a physician, respiratory therapist or nurse, patients receive volumes of gas per breath (tidal volume) which are too small and respiratory rates which are too quick. This has been shown to create significant adverse effects on patients.

Automatic ventilatory devices (ventilators) were originally developed to deliver a set amount of volume to the patient in a set amount of time which little patient monitoring capability. In the last 25 years different modes, including pressure control, and increased monitoring capabilities have been added, leading to the modern transport ventilators of today. Most ventilators still use volume and time cycled ventilation modes which operate by delivering to the patient pre-set amount of volumes or constant flow for pre-set amounts of time, regardless of the patient's lung compliance. Lung compliance is prone to sudden changes during transport, potentially causing patient airway pressures to increase to the point that they will severely injure the patient. Pressure cycled ventilation and pressure control are newer modes of ventilation used to deliver ventilatory support to the patient and which have a number of distinct advantages over volume and time cycled ventilation modes. Pressure cycled ventilation functions by switching to exhalation from inhalation when a certain pressure is reached, regardless of the volume delivered; thus volumes of gas delivered to the patient vary with variances in lung compliances, preventing the patient from receiving a harmful amount of pressure and insuring appropriate ventilation of the patient.

Modern transport ventilators are battery of pneumatically powered and equipped with numerous ventilation modes, including pressure cycled types of ventilation, various flow control functions, multiple alarm monitoring functions and are also capable of detecting and synchronizing with the patient's breathing efforts. Although current transport ventilators provide consistent, safe and reliable ventilation, they are extremely expensive. Additionally, the disposable accessories that are required to be used with these ventilators can sometimes cost as much or more than a manual resuscitator. To reduce the high capital costs of these devices, some manufacturers have returned to offering simplified time cycled volume ventilators without any of the standard monitoring, control and alarm features of typical ventilators, nor the option of pressure cycled ventilation. These devices are often classified as automatic resuscitators and, in addition to not being as safe, still cost thousands of dollars and require the use of additional disposable or parts which require sterilization before being reused. In today's environment of medical cost containment, hospitals and other medical providers have, for the most part, balked at the cost of transport ventilators and the training of additional personnel it would require.

A Pulmonary Modulator Apparatus (PMA), as described in U.S. Pat. No. 6,067,984 and included herein by reference in its entirety, has been shown to successfully solve the consistency problem of manual resuscitators and the capital expense issues of transport ventilators. Unfortunately a PMA has a number of problems: 1. it can stop cycling due to physiological, mechanical, pneumatic, or environmental changes; 2. it can be hard or impossible for a user to determine if the device is automatically cycling or if the patient is initiating breathing thus increasing the work of breathing for the patient; 3. it is limited to delivering a set level of PEEP that is a constant ratio of PIP; and 4. it has no means of providing an inspiratory hold.

As described in U.S. Pat. No. 6,067,984, a pressure pulmonary modulator apparatus (PMA) comprises a dual area piston (or diaphragm) having a surface area that rests against an interior end of a inlet chamber, thus sealing the inlet chamber during the inhalation phase of the patient. The dual area piston comprises a primary area defined as the area exposed to the patients pulmonary capacity during inspiration when the piston is in the closed position, and a much larger area which comprises the entire area of the piston which is in fluid communication with the patients pulmonary capacity only during discharge or when the piston is in the open position. When the dual area piston is closed, it prevents compressed gas from escaping and causing the lungs to become charged by the incoming compressed gas. During charging (i.e. inspiration), the pressure in the patients lungs increases until the force of the pressure on the primary area of the dual area piston overcomes the restorative force of the piston. Once the dual area piston begins to open, the full area of the piston is exposed to the pressure of the patient's lungs causing the piston to move away from the interior end of the inlet chamber to a fully open position almost immediately. The patient's lung pressure that causes the piston to move into the fully open position is the patient's peak inspiratory pressure (PIP), which is adjustable by controlling the restorative force on the piston. Once the piston opens, it will remain open until the patient's lung pressure drops to a value small enough such that the restorative force overcomes the force of the patient's lung pressure on the full area of the piston. During discharge, the exhaled gases pass by the piston and out of the system through an adjustable flow restrictor (i.e. the rate dial) used to control the rate at which discharge gases are vented into the atmosphere, resulting in the control of discharge duration. The rate dial is essentially a valve, and resistance to exhalation flow is realized by screwing or adjusting the rate dial in our out. Greater resistance to flow results in slower exhalation flows and longer exhalation times. Once the patients lung pressure drops to a value low enough to allow the force of the spring to push the piston closed, the discharge ends and the cycle is repeated.

The patient may spontaneously breathe by triggering the inhalation prior to the end of exhalation. A one-way valve may optionally be provided to increase the ease of the patient's inhalation. Under such circumstances, a new inhalation will start when the patient breathes in, reducing the patient's airway pressure and causing the piston to close and a new inhalation period to start. In addition, the apparatus can be adapted to function as a positive pressure aerosol device by attaching a nebulizer assembly to the inlet chamber of the apparatus. Such a device is useful to those needing the therapeutic effects of aerosol in addition to ventilatory support.

From time to time it may be useful to put the PMA into a "spontaneous mode" in which inspiration starts only after the patient has initiated it by drawing a breath. This mode is achieved by dialing the rate dial to such a position that the restriction to flow for the set flow of gas provided creates an internal pressure great enough that it maintains a greater force on the open piston/diaphragm than the restorative spring force. In such a condition inhalation is initiated by the patient inhaling enough gas that the pressure drops and the restorative force of the spring causes the piston/diaphragm to close.

A PMA can stop cycling, and thus stop providing ventilatory support to a patient, due to physiological, mechanical, pneumatic, or environmental changes. Although this has the benefit of alerting the clinician that the situation is changing, the condition is ultimately highly undesirable because the patient still needs ventilatory support and the only manner that ventilatory support may be provided by existing PMAs is by the clinician determining what change occurred and changing the baseline settings of the PMA to compensate. Determining what change occurred can be time consuming, and if the patient is not being provided ventilatory support, clinicians are rushed and almost always don't have the time. Furthermore, changing the baseline settings of the PMA is often undesirable because it creates a greater degree of uncertainty in a situation that may still be varying and problematic, thus re-stabilizing the patient becomes more difficult. Therefore there is a need for a device with the advantages of a PMA that has the further capability of delivering temporary or alternate ventilatory support regardless of physiological, mechanical, pneumatic, or environmental changes and without changing the baseline settings of the PMA.

Under most circumstances, a PMA is used with a patient who is unconscious and paralyzed due to the administration of medication by the clinician. The sedation of the patient is necessary because it mitigates the risk that the patients will become hypertensive and fight the ventilatory support of the PMA, or that the patient will simply begin to hyper-ventilate. Maintaining the patient in a sedated state can sometimes be problematic because the effects of the medication can subside, or if the medication has just recently been administered, it will take time for the medication to take effect. Much of the time patients are transitioning from one sedated state to another. In the interests of stabilizing the patient, insuring that the work of breathing is appropriate for the patient, and allowing the clinician to address other possible patient conditions, it is important for the clinician to be able to determine if the patient is truly sedated, and that the breathing of the patient is purely caused by the PMA, or if the patient is still semi-active on a respiratory basis and is triggering the device with slight inhalation efforts. Determining which state the patient is in is very difficult to do with the existing PMA design because it is impossible to tell if the patient or the device is causing the cycling of the PMA. Therefore there is a need for a device with the advantages of a PMA that has the additional capability of providing some feedback to the clinician on the sedative state of the patient.

Current PMAs have an intrinsic design PEEP for any set PIP. Since some patients may require additional PEEP beyond what is provided for a set PIP, this is a serious limitation of the PMA. Currently, the PMA may be set to deliver an increased PEEP by adjustment of the rate dial or by increasing flow, but this places the device in a mode that will not cycle unless initiated by the patient which is clearly undesirable the vast majority of the time because it increases the work of breathing of the patient and the patient may simply be unable to make the respiratory effort. The situation can be rectified by addition of an in-line PEEP valve placed between the inlet of the modulator and the patient's airway, but this adds to the cost and clumsiness of the device, and is not practical since additional PEEP is only needed sometimes and as a result clinicians are not likely to keep such devices on hand. Therefore, there is a need for a device with the benefits of existing PMAs that had the additional capability of delivering more PEEP when desired.

Sometimes there is a need for the clinician or user to create an inspiratory hold which is effectively a pause at approximately the peak pressure of inspiration before the initiation of exhalation, or to simply suspend ventilatory support temporarily. An inspiratory hold (clinically also sometimes referred to as sigh breath) can provide important physiological support of certain types of patients. A pause in ventilatory support can provide a needed opportunity for a clinician to perform a needed procedure without the interference of on-going ventilation. Current PMAs do not have this capacity without inducing major clinical inconvenience and disturbance. One method currently employed using existing PMAs is to create a condition in which the entire exhalation path is occluded, potentially leading to damaging pressure levels, and failing to provide a sustained pressure level support. Another is to remove the modulator from patient tee thus eliminating any pressure support of the patient and risking alveolar collapse. Therefore, there is a need for a device with the benefits of existing PMAs that has the additional capacity of delivering an inspiratory hold, or ventilatory pause, in a manner that will limit the pressure level and will not entirely occlude the exhalation path of the patient.

In the pre-hospital environment, many of the Emergency Medical Technicians (EMTs) servicing patients during emergency calls do not have the same sophistication and training as Respiratory Therapists and clinicians in the hospitals. As a result, there is sometimes a reluctance to employ existing PMAs because there is a fear that the EMT may face a situation in which they are not entirely sure what the most appropriate adjustment would be in the event that the PMA stops delivering ventilatory support for mechanical or physiological reasons. Existing PMAs don't have any readily available way to provide these clinicians with a simple back up plan in such event. Therefore, there is a need for a device with the benefits of existing PMAs that has the additional capacity of providing a simple back up plan to clinicians unsure of the changing situation they may be facing.

The present invention has all the benefits of existing PMAs with the added benefit of solving the previously described problems. Specifically the current invention has the advantage that it will: 1. deliver immediate manually triggered ventilatory support regardless of any changes that may have stopped the PMA from automatically cycling (i.e. delivering automatic ventilatory support); 2. provide valuable feedback to the clinician on the sedative/conscious state of the patient; 3. deliver more PEEP than the intrinsic design PEEP of the PMA for the given PIP and flow setting; 4. deliver an inspiratory hold, or ventilatory pause, in a manner that will limit the pressure level and will not entirely occlude the exhalation path of the patient when desired by the clinician; and 5. provides a simple back up plan that still provides ventilatory support to patients for clinicians unsure of the mechanical and physiological situation they are facing.

SUMMARY OF THE INVENTION

The present invention generally comprises a pressure pulmonary modulator apparatus which will inflate and discharge any respiratory gas from a patient for a wide range of frequencies when provided with a constant flow of gas and which also has the ability to immediately provide inhalation support to a patient at a limited finite level of pressure whenever manually actuated by the clinician while requiring no more parts or cost than existing PMAs.

An object of the invention is to provide a simplified ventilator apparatus for providing constant flow, pressure cycled ventilatory support to patients and that allows immediate manual initiation of inspiration support.

Another object of the invention is to provide a simplified ventilator apparatus that provides constant flow, pressure cycled ventilatory support and that allows for easy detection of the sedative state of the patient.

Another object of the invention is to provide a simplified ventilator apparatus for providing constant flow, pressure cycled ventilatory support and that allows for easy detection of whether the device is in an automatic cycling or spontaneous mode.

Another object of the invention is to provide a simplified ventilator apparatus for providing constant flow, pressure cycled ventilatory support to children and adults in an emergency situation that allows for higher PEEP settings.

Another object of the invention is to provide a simplified ventilator apparatus for providing constant flow, pressure cycled ventilatory support to children and adults in an emergency situation that allows the clinician or user to hold a longer inspiration time.

Another object of the invention is to provide a ventilator apparatus which is disposable and inexpensive.

Another object of the invention is to provide a ventilator apparatus which allows for the adjustment of peak pressure, positive end expiratory pressure, inspiration duration, and expiration duration.

Another object of the invention is to provide a ventilator apparatus which can allow the patient to trigger mandatory breaths or to breathe spontaneously.

Another object of the invention is to provide a ventilator apparatus which can allow the patient to breathe spontaneously entirely, with manual interjections of inspiration by the clinician or user.

Another object of the invention is to provide a ventilator apparatus which allows inhalation to be initiated by the operator of the apparatus.

Another object of the invention is to provide a ventilator apparatus which can be equipped, or have a built-in high pressure pop-off valve as a safety feature to prevent the unintended build up of patient airway pressure due to malfunction or misuse. Such a high pressure pop-off valve may be equipped with the means to produce an audible tone which will notify an operator that the patient is experiencing high airway pressures.

Another object of the invention is to provide a ventilator apparatus which can be easily used in conjunction with a nebulizer to deliver intermittent positive pressure aerosolized medication to the patient at high and low respiratory rates.

Another object of the invention is to provide a ventilator apparatus which can deliver ventilatory support to patients being transported within or between hospitals.

Another object of the invention is to provide a ventilator apparatus which can be used to treat patients suffering from sleep apnea.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more easily understood by a detailed explanation of the invention including drawings. Accordingly, drawings which are particularly suited for explaining the inventions are attached herewith; however, it should be understood that such drawings are for descriptive purposes only and as thus are not necessarily to scale beyond the measurements provided. The drawings are briefly described as follows.

LIST OF REFERENCE NUMERALS

Figure 1:
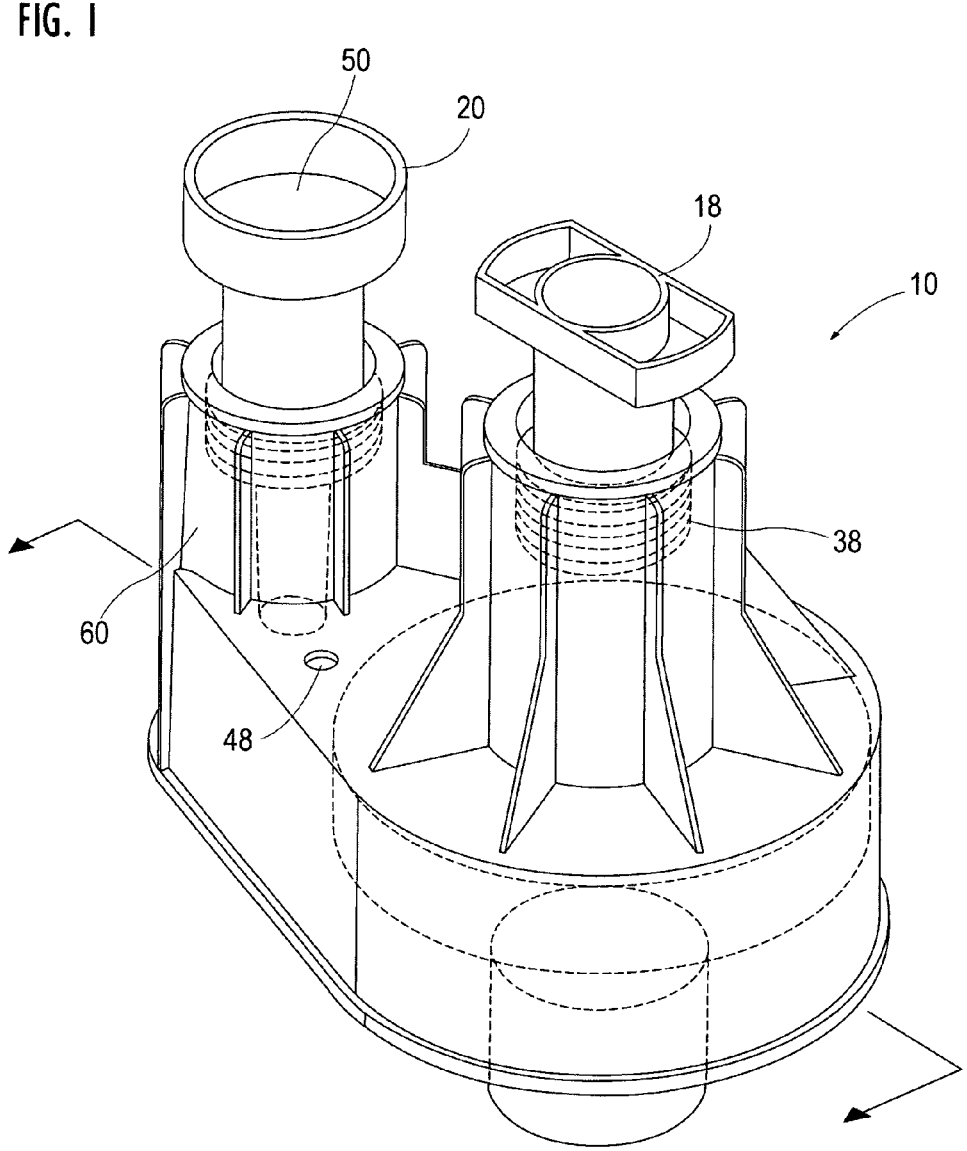
FIG. 1 is a perspective view of a pressure modulator apparatus in accordance with the present invention.

10 Pressure Modulator Apparatus
12 Diaphragm Assembly
14 Inlet Chamber
16 Flow Restrictor Conduit
18 Pressure Dial
20 Rate Dial
22 Modulator Housing
24 Modulator Base
26 Diaphragm Plate
27 Diaphragm Ring
28 Interior End
30 Spring
32 Spring Boss
34 External Threads
36 Internal Threads
38 Pressure Dial Boss
40 Cylindrical Sleeve
42 Primary Modulator Chamber
44 Equalization Conduit
46 Secondary Modulator Chamber
48 Safety Discharge Orifice
50 Rate Dial Exhaust Port
52 Flow Restrictor Valve Seat
54 Slots
55 Tapered Inner End
56 External Threads
58 Internal Threads
60 Rate Dial Boss
62 Sealing Ring
64 Ambient Actuation Conduit
66 Patient Adapter
68 Attachment Port
70 Pop-Off Valve
70 Pop-Off Valve
72 Patient Demand Valve
74 Gas Inlet Port
76 Patient Connection Port
80 Flapper
82 One-Way Valve Port
84 Valve Body
86 Face Mask
88 Pop-Off Spring
90 Pop-Off Piston
92 Pop-Off Housing
94 Piston Ring
96 Piston Seal
98 Piston Base
100 Piston Ring Orifice
102 Piston Seal Orifice
104 Piston Base Orifice
106 Second Pressure Dial
108 Ambient Actuation Conduit
110 Third Pulmonary Modulator Apparatus
112 Long Diaphragm
114 Outer Spring
116 Sealing O-ring
118 Equalization Conduit
120 Ambient Actuation Conduit
122 Third Pressure Dial
124 Third Inlet Chamber
126 Third Modulator Body
128 Primary Modulator Chamber
130 Secondary Modulator Chamber

DETAILED DESCRIPTION OF THE INVENTION

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

For illustrative purposes the present invention is embodied in the apparati generally shown in FIG. 1 through 7. It will be appreciated that the apparatus may vary as to configuration and as to details in the parts without departing from the basic concepts as disclosed herein.

Figure 2:
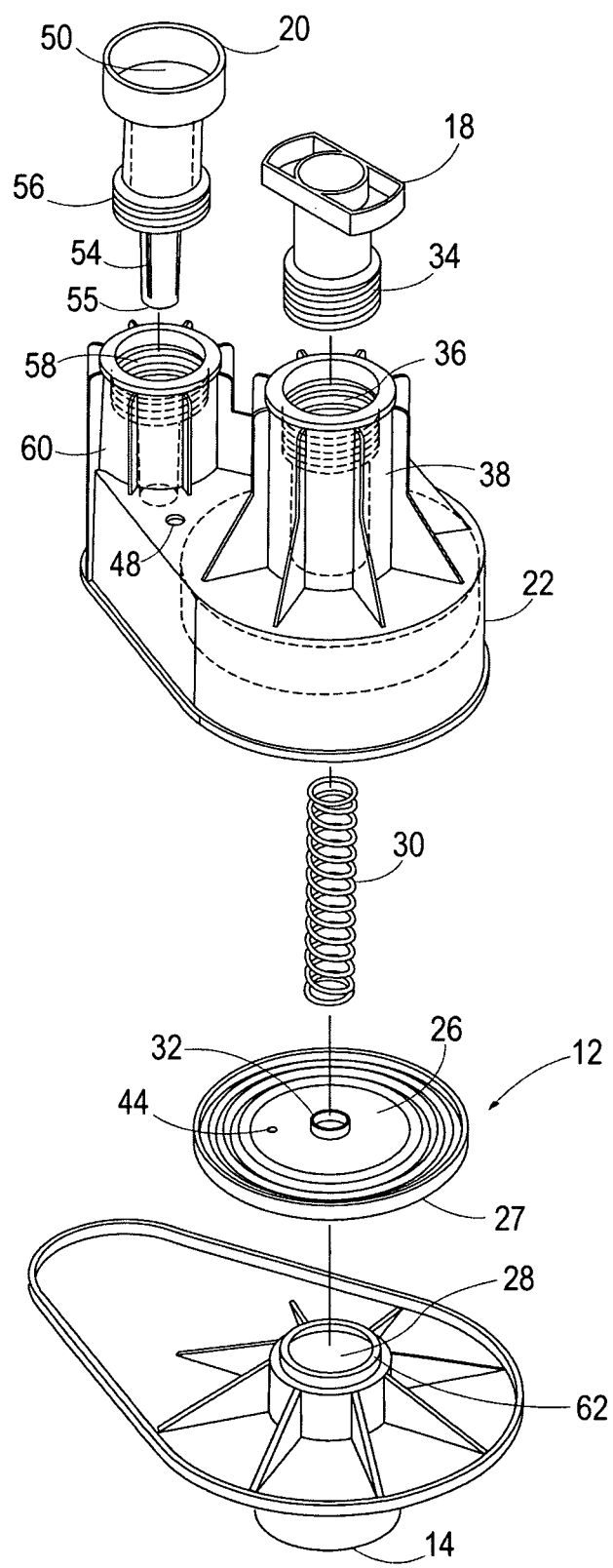
FIG. 2 is an exploded perspective view of the apparatus shown in FIG. 1.
Figure 3:
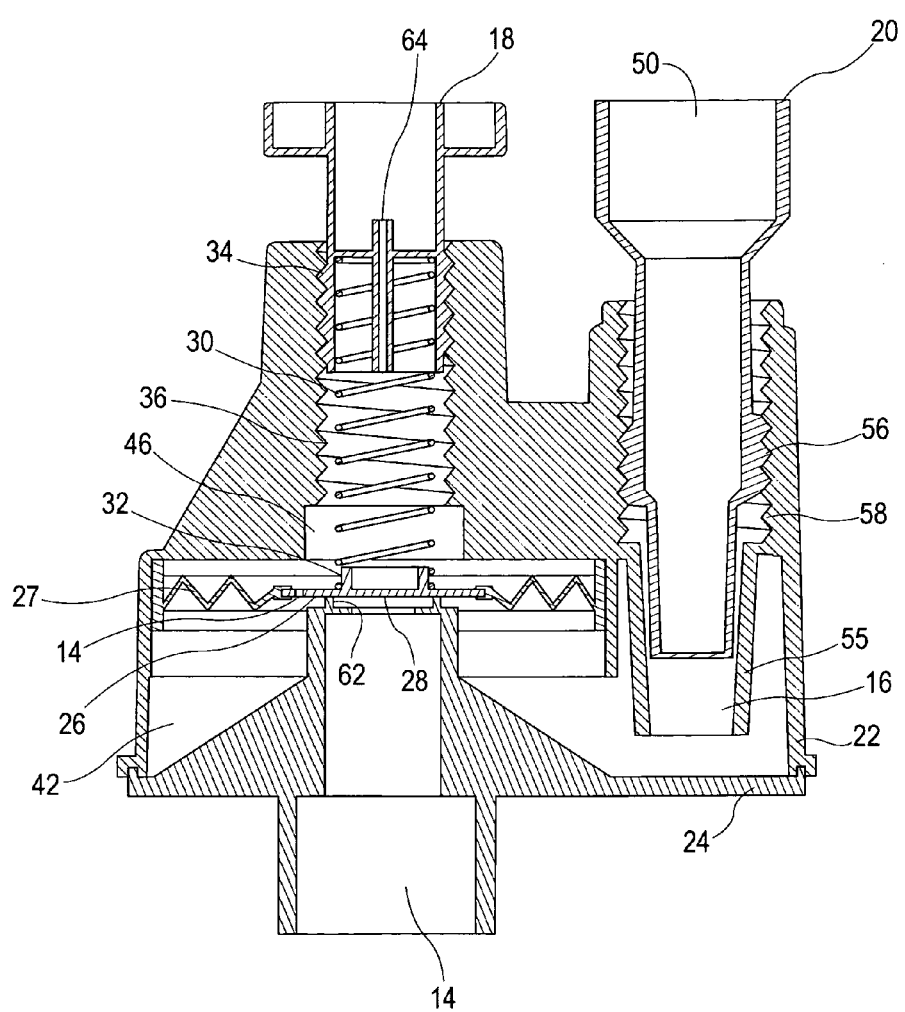
FIG. 3 is a sectional view of the apparatus shown in FIG. 1.
Figure 4:
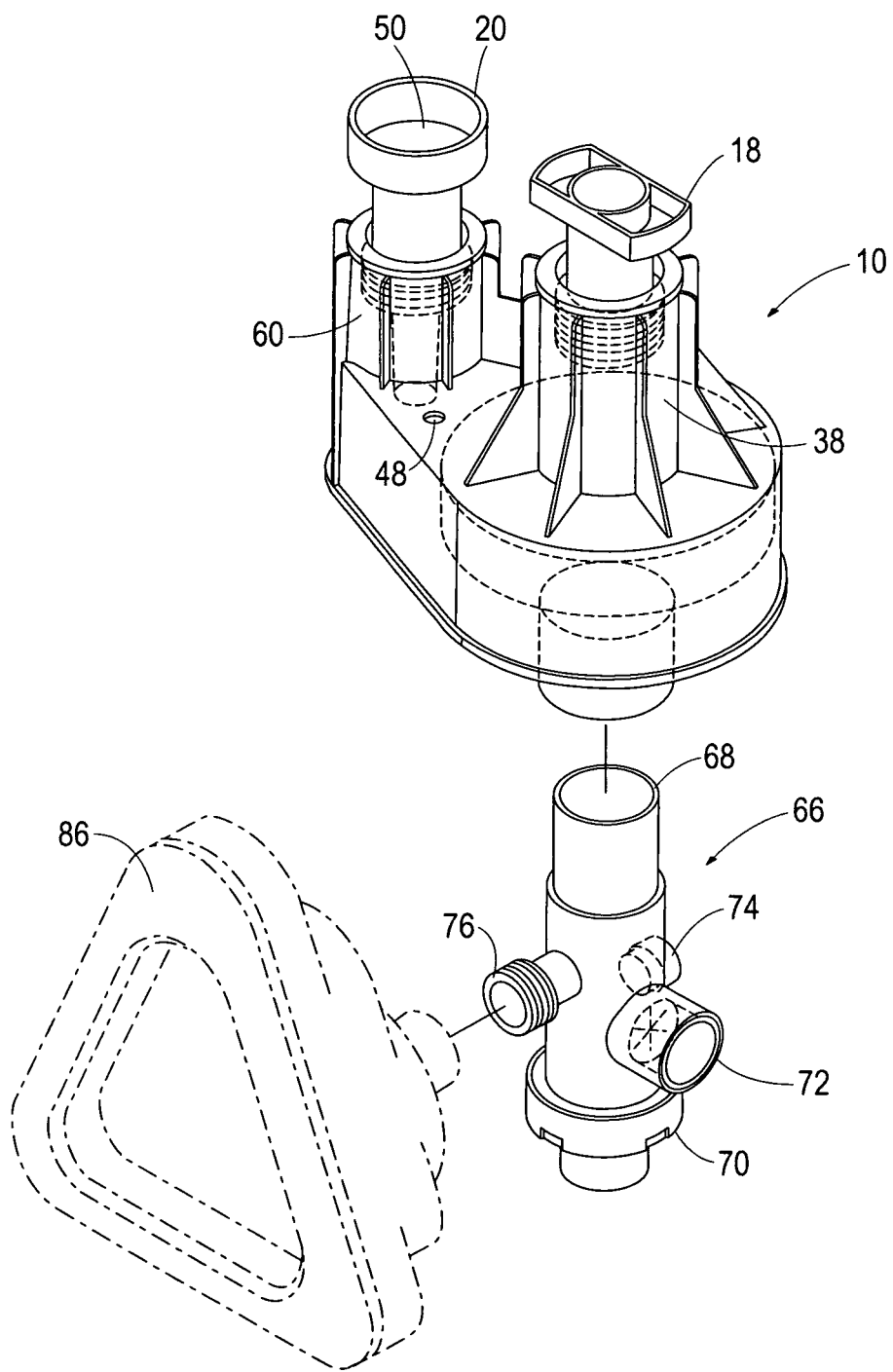
FIG. 4 is an exploded perspective view of the apparatus shown in FIG. 1 and a patient tee adapter in accordance with the invention adapted to function as a resuscitation device with a face mask shown in phantom.
Figure 5:
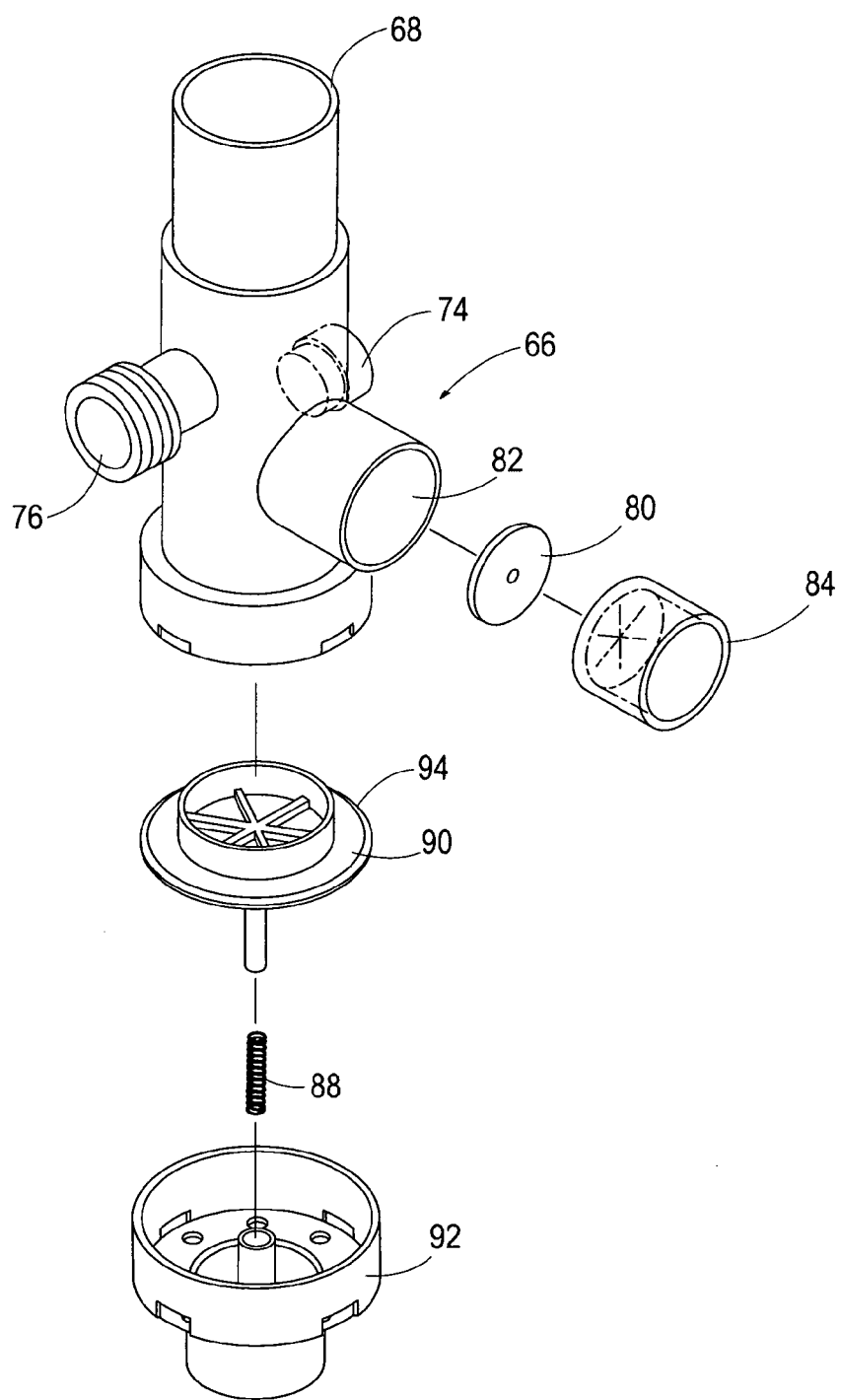
FIG. 5 is an exploded perspective view of patient tee adapter shown in FIG. 4.

Referring first to FIG. 1, FIG. 2, and FIG. 3 a constant flow, pressure modulator apparatus 10 in accordance with the preferred embodiment of the present invention is generally shown. As will be seen, the apparatus comprises a spring-loaded diaphragm assembly 12, an inlet chamber 14, a flow restrictor conduit 16, a pressure dial 18, a rate dial 20, a modulator housing 22 and modulator base 24. The apparatus of the preferred embodiment is fabricated almost completely of injection molded plastic.

Diaphragm assembly 12 consists of a center diaphragm plate 26 which is captured circumferentially by diaphragm ring 27. Diaphragm assembly 12 is normally biased in a close position wherein the diaphragm plate 26 rests against the interior end 28 of inlet chamber 14. A spring 30 is located around a spring boss 32 which maintains spring 30 in a substantially perpendicular orientation relative to diaphragm plate 26. External threads 34 on pressure-dial 18 engage internal threads 36 within the pressure dial boss 38, which is located atop modulator housing 22. Rotating pressure dial 18 causes pressure dial 18 to move longitudinally relative to diaphragm plate 26, thereby increasing the compressive force on spring 30 as pressure dial 18 is moved closer to diaphragm plate 26. Pressure dial 18 therefore allows adjustment of the compressive force of spring 30 against diaphragm assembly 12. Diaphragm plate 26 moves longitudinally within a cylindrical sleeve 40 located within assembly of modulator housing 22 and is in flow connection with a primary modulator chamber 42 formed by the assembly of modulator housing 22 and modulator base 24. Diaphragm ring 27 can be made of a variety of rubber like compounds but is usually made of silicone plastic or more preferably santoprene, and is pleated so that longitudinal movement of diaphragm plate 26 is minimally restricted. The outer diameter of diaphragm ring 27 is so sized that when inserted into cylindrical sleeve 40 during assembly an airtight seal is formed. Although the outer diameter of diaphragm ring 27 and cylindrical sleeve 40 have been described as round and cylindrical, those skilled in the art can see that other profile shapes are possible without departing from the nature and essence of the invention.

Flow restrictor port 16 is located within modulator housing 22 and is in flow connection with primary modulator chamber 42. Rate dial 20 allows for adjustment of the rate of gas escaping from modulator chamber 42 to the atmosphere, and adjusting rate dial 20 allows control of a patient's exhalation duration and PEEP. An annular flow restrictor valve seat 52 is located within flow restrictor port 16. Flow restrictor valve seat 52 functions in conjunction with tapered inner end 55 of rate dial 20 to restrict gas from passing through flow restrictor port 16. Slots 54 in rate dial 20 have a much larger cross-sectional area than flow restrictor port 16 at its largest setting and poses little restriction to flow. The restricting area between flow restrictor valve seat 52 and the tapered inner end 55 of rate dial 20 is adjustable by positioning rate dial 20 axially through use of external threads 56 on rate dial 20 which engage internal threads 58 within the rate dial boss 60, whereby rotating rate dial 20 causes tapered inner end 55 to move longitudinally relative to flow restrictor valve seat 52. Flow restrictor valve seat 52 and tapered inner end 55 at the inner end of rate dial 20 functions similar to a needle valve to create a restrictive annular region to restrict the flow of gas there through. Slots 54 remain of constant cross-sectional area throughout the adjustment range of rate dial 20. Use of tapered inner end 55 and annular valve seat 52 provides for a sensitive adjustment of gas flow resistance. Although the preferred embodiment discloses using a tapered inner end 55 of rate dial 20 with slots 54 therein along with flow restrictor valve seat 52 to restrict gas flow there through, those skilled in the art would recognize that other means for providing adjustable gas flow resistance exist. As an additional safety feature and protection for the patient against the possibility of the rate dial exhaust port 50 becoming occluded, and thereby exposing the patient to dangerous levels of pressure, an additional safety discharge orifice 48 may be placed in the modulator body allowing a secondary escape of gas from the primary modulator chamber 22. Said safety discharge orifice 48 may be place anywhere in the modulator body provided it creates the means for fluid communication between primary modulator chamber 22 and the ambient environment. The safety discharge orifice 48 is so sized to not provide so great a discharge of gas as to prevent the adjustment of the PMA to needed exhalation times of up to 5 seconds or more, but is large enough so provide a relief of gas in the event that the rate dial exhaust port 50 is occluded. In practice, safety discharge orifice 48 is approximately 0.125" in diameter.

During the patient inspiration, diaphragm plate 26 rests against interior end 28 of inlet chamber 14. This constitutes diaphragm assembly, consisting of diaphragm plate 26 and diaphragm ring 27, being in a closed position. A sealing ring 62 circumscribing interior end 28 of inlet chamber 14 provides an airtight seal when diaphragm plate 26 rests against interior end 28 of inlet chamber 14. While diaphragm plate 26 is resting against interior end 28 of inlet chamber 14, the force of the patient's pressure on diaphragm plate 26 is equal to the product of the patient's pressure and the area circumscribed by sealing ring 62. As the patient inhalation develops and the patient is charged, the patient's pressure will increase until the force of the patient's airway pressure on diaphragm plate 26 overcomes the compressive force of spring 30, which causes diaphragm assembly to open (i.e. diaphragm plate 26 moves away from interior end 28 of inlet chamber 14).

Diaphragm plate 26 includes equalization conduit 44 that provides the intended fluid path between primary modulator chamber 42 and secondary modulator chamber 46. Equalization conduit 44 works optimally for the described embodiment if in the diameter range of 0.030" to 0.050", but has been shown to continue to perform for diameters as small as 0.010" and as large as 0.125". Larger sizes may also be possible, but can be less desirable because bigger sizes begin to limit the PMA to smaller exhalation times than may be desired by the clinician. Although equalization conduit 44 is described herein as round, the actual shape is irrelevant provided that the equivalent cross sectional area is made available for the flow of gas between primary modulator chamber 42 and secondary modulator chamber 46. Furthermore, multiple orifices, or multiple other cross sectional flow shapes can be utilized if desired without departing from what is described, and equivalent performance would be expected provided that the sum of the cross-sectional flow areas is equal to the cross-sectional area of a single equalization conduit 44.

Secondary modulator chamber 46 is the enclosed spaced encompassed by the modulator housing 22, pressure dial 18, diaphragm plate 26, and diaphragm ring 27. An intrinsic property of secondary modulator chamber 46 is that internal pressure within secondary modulator chamber 46 creates a force on the sealing member of the modulator (in this embodiment diaphragm plate 26) that is in the same direction as the biasing force (in this embodiment spring 30) on the sealing member of the modulator towards the closed position, and which is also in opposition to the resulting force on the sealing member of the modulator as a result of the internal pressure in primary modulator chamber 42.

Referring to FIG. 3 ambient actuation conduit 64 is shown in pressure dial 18. Ambient actuation conduit 64 provides fluid communication between secondary modulator chamber 46 and the ambient environment. When ambient actuation conduit 64 is un-occluded pressure modulator apparatus 10 provides ventilatory support as previously described, and as is normal for other PMAs. In the event that the clinician places his or her finger over the pressure dial, this will cause the occlusion of ambient actuation conduit 64. When ambient actuation conduit 64 becomes occluded the pressure in secondary modulator chamber 46 is allowed to rise, thus providing additional force on diaphragm plate 26 in the same direction of the biasing force of spring 30, and thus the pulmonary modulator apparatus 10 closes. Upon the pulmonary modulator apparatus 10 closing, the patient will begin to be charged with gas and the patient's airway pressure will rise until such time that the force of the patient's pressure on diaphragm plate 26, circumscribed by the sealing ring 62, overcomes the force of spring 30. While ambient actuation conduit 64 is occluded, the pressure differential between primary modulator chamber 42 and secondary modulator chamber 46 are minimized through the fluid communication provided by equalization conduit 44. So long as this is the case, pulmonary modulator apparatus 10 can not behave as a dual area valve that opens at one pressure and closes at another lower pressure, thus cyclical ventilatory support is not provided by pulmonary modulator apparatus 10, and, upon the patient's airway pressure reaching sufficient value to overcome spring 30, the diaphragm plate 26 will move away from sealing ring 62 of just sufficient distance for the patient's airway pressure to be maintained at a constant value approximately equal to the patient pressure sufficient to overcome spring 30. The ambient actuation conduit 64 need not necessarily be in the pressure dial, and may be placed anywhere provided that it allow fluid communication between secondary modulator chamber 46 and the ambient environment and have some means of being occluded, either directly by the clinician's finger, or by some other mechanical means or apparatus. The current embodiment uses a circular cross-sectional shaped ambient actuation conduit 64 that is approximately 2.5 times greater in diameter than equalization conduit 44, but a wide range of sizes would be sufficient and work equally as well as what is described herein provided that they are larger in cross sectional area than equalization conduit 44 and that they may in some manner or form be occluded by the clinician. As with equalization conduit 44, the exact shape and number of conduits used to form ambient actuation conduit 64 are not as important as the total combined cross-sectional area and the means to be occluded by the clinician. Of additional importance is that external threads 34 and internal threads 36 be of sufficient fit to prevent undue leaking of gas from secondary modulator chamber 46 into the ambient environment thus having a detrimental effect on the operation of ambient actuation conduit 64.

Referring again to FIG. 4 pressure modulator apparatus 10 and a patient adapter 66 are shown combined together to function as an automatic resuscitator or ventilator. Patient adapter 66 is attached to inlet chamber 14 of pressure pulmonary modulator apparatus 10 via attachment port 68. Patient adapter 66 is equipped with a pop-off valve 70, a patient demand valve 72, a gas inlet port 74 and a patient connection port 76. The combination of pressure modulator apparatus 10 and patient adapter 66 serves as a automatic resuscitator or ventilator which may be interface with a face mask 80, as shown in phantom, or an endotracheal tube.

Gas inlet port 74 allows connection to a source of compressed gas (not shown), such as compressed air or oxygen. The compressed gas source is attached to gas inlet port 74 using a DISS connector, barb, or snap connection (not shown). Internal to gas inlet 74 is an orifice sized to ensure that for an approximate 50 psig compressed gas source, the flow will not exceed approximately 40 liters/minute. Typically, the compressed gas would consist entirely of 100% compressed oxygen but a clinician may use any type of compressed gas as deemed appropriate. The compressed air or oxygen is delivered directly to the patient for inhalation. Gas inlet port 74 can also be so configured that the exiting jet emitting from the sized orifice entrains room air through ports positioned adjacent to said orifice, thus 15 l/min of oxygen may result in delivery of an air oxygen mixture to the patient at a combined rate of 40 l/min.

Patient demand valve 72 is a one-way valve, comprising of a flapper 80 placed between a one-way valve port 82 and a valve body 84, which allows air to be entrained from the room environment. Patient demand valve 72 allows the patient to draw in more air than that which is being continuously supplied to patient adapter 66 through gas inlet port 74 from the compressed gas source, thus giving the patient not only the means to initiate the beginning of inhalation but also the duration. In the preferred embodiment, patient demand valve 72 has a very low resistance to flow, which is on the order of approximately 3.5 cm $H_2O$ at 50 liters/minute.

Pop-off valve 70 provides a safety feature to prevent the patient airway pressure from exceeding any set, or pre-set, value and consists of pop-off spring 88, pop-off piston 90, and pop-off housing 92. Pop-off piston 90 is biased by pop-off spring 88 and equipped with a sealing edge 94. Pop-off valve 70 opens anytime the patient's airway pressure exceeds a preset value whereby the force of the patient's pressure on pop-off piston 70 overcomes the bias and restorative force of pop-off spring 88. Pop-off valve 70 can be equipped with a means to create an audible tone and a visual signal when the valve 70 is opened. Although Pop-off valve 70 provides a needed back up pressure relief, it is set at a high enough value that pressure reached to cause it to open may still be dangerous to some patients. Another embodiment of the invention, and one that will result in less parts, is to combine patient demand valve 72 into pop-off valve 70. Such an embodiment includes equipping pop-off piston 90 with fluid conduits and a flapper that preferentially allow flow into, but not out of, patient adapter 66.

Patient connection port 76 allows a connection of a breathing mask 86, an endotracheal tube (not shown), or a laryngeal mask airway (also not shown) which the patient wears during the breathing process associated with resuscitator 78. Because the pulmonary modulator apparatus 10 is closed during inhalation, all incoming gas is delivered to the patient through patient connection port 76. In the preferred embodiment, patient connection port 76 has a 22 mm OD for connection to PEEP masks (not shown) and a 15 mm ID for connection to endotracheal tubes.

When inhalation pressure reaches that which is dialed on pressure dial 18, diaphragm plate 26 moves to the fully open position, the patients peak pressure (PIP) to the patients baseline pressure (PEEP) is 10:1, which is consistent with the ratio of the full surface area of diaphragm assembly in pulmonary modulator apparatus 10 and the surface area circumscribed by sealing ring 62. Pressure dial 18 and pulmonary modulator spring 30 are designed so that the resuscitator delivers a maximum patient peak pressure (PIP) of approximately 55 cm $H_2O$ and a minimum PIP of approximately 10 cm $H_2O$, although these pressures and the referred ratio are not the physical limit of the apparatus. Pop-off valve 70 is designed to relieve pressure if the patient's airway pressure rises above approximately 60 cm $H_2O$.

Thereby the present invention provides the means for a user to initiate inhalation immediately without changing any baseline settings of the device whenever the invention stops providing ventilatory support (i.e. stalls) regardless if the device stopped cycling due to changes in physiological, mechanical, pneumatic or environmental conditions, by simply occluding ambient actuation conduit 64. Thereby the present invention is capable of being used by a user to determine the sedative state of a patient by adjusting the device to the spontaneous mode and satisfying oneself that the device only initiates inhalation when ambient actuation conduit 64 is occluded. Thereby the present invention is capable of higher PEEP settings than are otherwise possible by increasing the rate dial setting such that the restriction to flow and the continuous flow of gas provides the desired PEEP pressure, causing the device to be in a spontaneous mode, whereby the user causes cycling of the device by periodically occluding ambient actuation conduit 64. Thereby the present invention is capable of providing an inspiratory hold by the user occluding and holding ambient actuation conduit 64 for the desired time. Thereby the present invention provides a reliable and simple alternative ventilatory support mode requiring less sophistication by the user and which is realized by the user simply occluding ambient actuation conduit 64 periodically whenever inhalation is desired, and releasing ambient actuation conduit 64 whenever exhalation is desired.

Figure 6A:
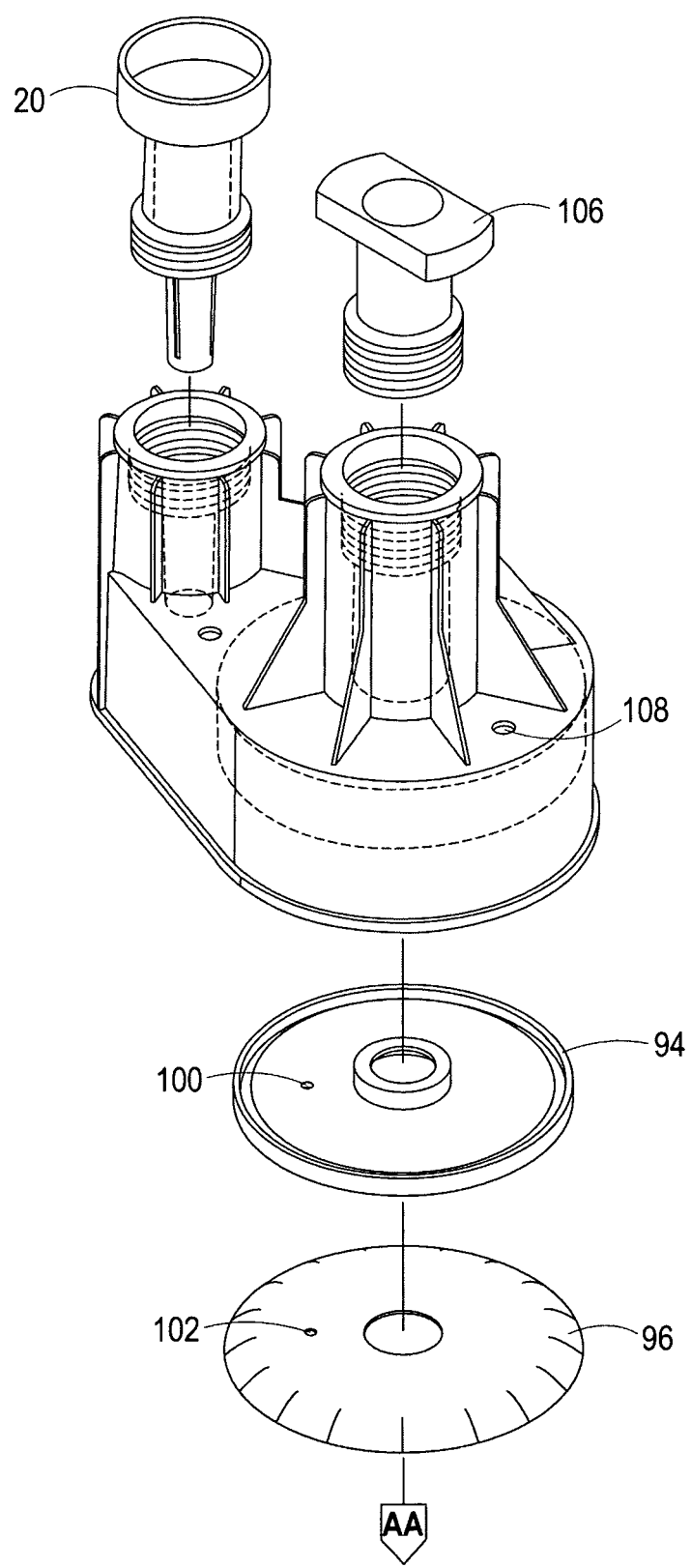
FIGS. 6A and 6B are an exploded perspective view of a pressure modulator apparatus in accordance with the present invention.
Figure 6B:
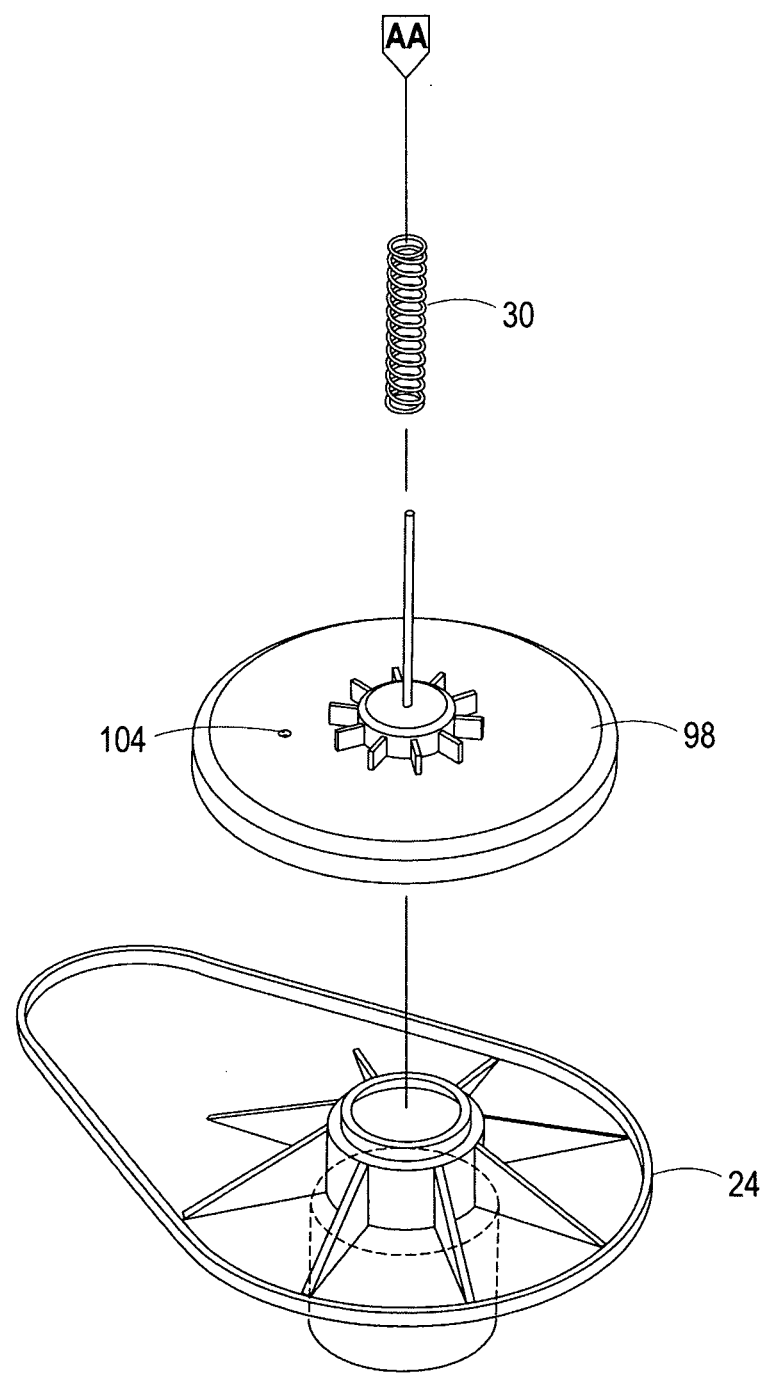

Referring to FIG. 6A and FIG. 6B is shown an alternative embodiment to pulmonary modulator apparatus 10. Instead of a diaphragm assembly using diaphragm plate 26 and diaphragm ring 27, the referenced alternative embodiment uses a piston assembly consisting of piston ring 94 and a piston seal 96 which is preferably made of a polyethylene or like material, and piston base 98. Piston seal 96 is placed over piston base 98 and is held in place by piston, ring 94 that is placed over piston seal 96 and caused to be snapped and held into place in reference to piston base 98. An equalization conduit is caused by aligning during assembly piston ring orifice 100, piston seal orifice 102, and piston base orifice 104 such that fluid communication is possible between the primary and secondary modulator chambers of the shown alternative embodiment. Alternative second pressure dial 106 is not equipped with fluid communication means that allow flow communication between the secondary modulator chamber and the ambient environment, instead means are provided by the alternative placement of ambient actuation conduit 108 that is placed in the modulator body as shown, and which functions identically as described in the first and preferred embodiment. With the exception of the inventive concepts described herein, further details of this embodiment are already known in the art and reference is made to U.S. Pat. No. 6,067,984.

Figure 7:
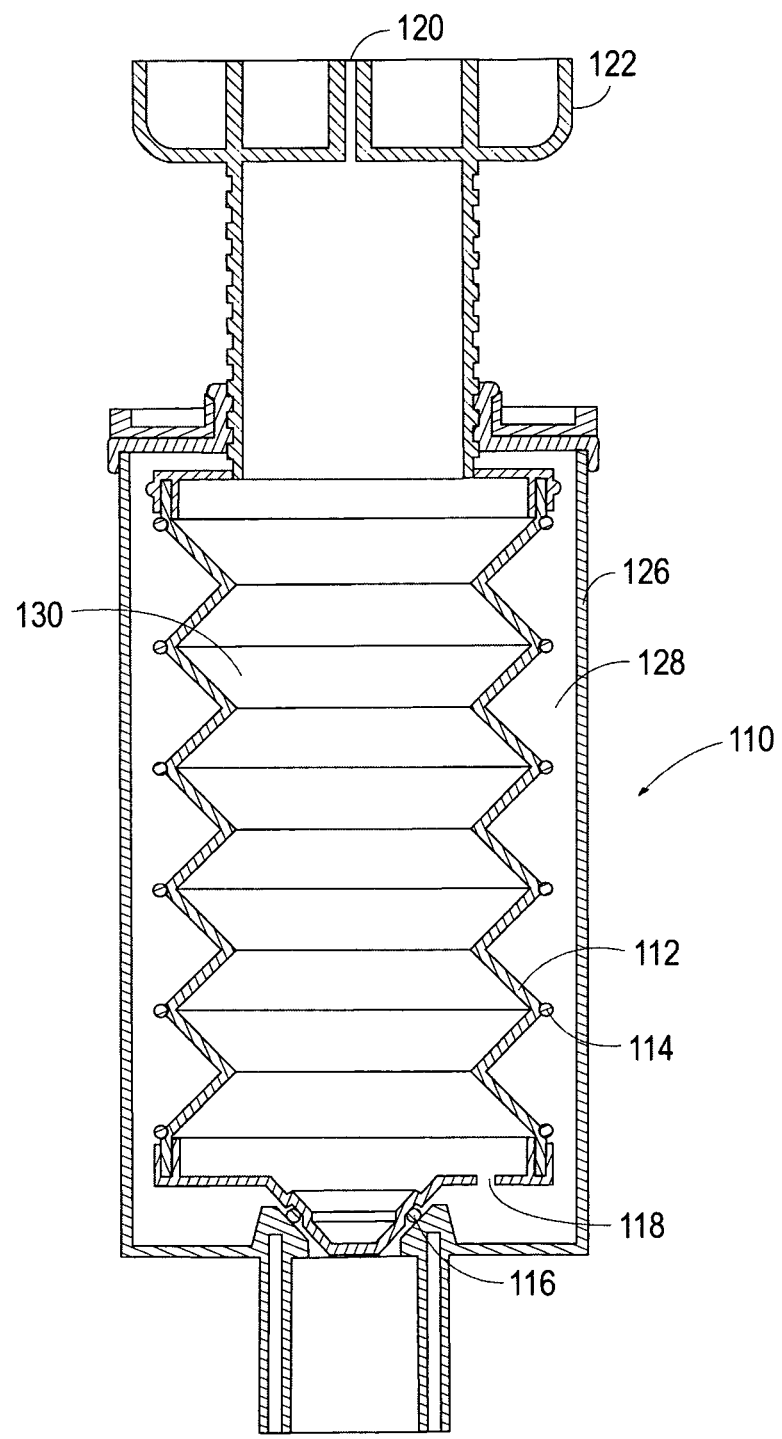
FIG. 7 is a sectional view of a pressure modulator apparatus in accordance with the present invention.

Referring to FIG. 7 is shown an alternative embodiment to pulmonary modulator apparatus 10. Third pulmonary modulator apparatus 110 consists of a long diaphragm 112, outer spring 114, sealing o-ring 116, equalization conduit 118, ambient actuation conduit 120, third pressure dial 122, third inlet chamber 124, third modulator body 126, primary modulator chamber 128, and secondary modulator chamber 130. With the exception of the inventive concepts described herein, further details of this embodiment are already known in the art and reference is made to U.S. Pat. No. 6,067,984.

Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A device for providing ventilatory support of a patient, comprising:
   a. a inlet chamber having an interior end and an exterior end;
   b. a valve, said valve including a first actuation area in flow communication with said inlet chamber when said interior end is closed by said valve, said valve including a second actuation area in flow communication with said inlet chamber when said interior end is open, said first actuation area being less than said second actuation area, wherein said valve is configured to open and close by changes in flow pressure applied to said inlet chamber, and wherein the pressure required to open said valve is greater than the pressure required to hold said valve open;
   c. a biasing member that provides a restorative biasing force on said valve, wherein said valve is normally biased in a position wherein said inlet chamber is closed, and wherein said pressure applied to said inlet chamber opposes said restorative biasing force;
   d. a primary chamber, said primary chamber in flow communication with said inlet chamber when said interior end is open, and wherein said primary chamber is not in flow communication with said inlet chamber when said interior end is closed, and wherein said primary chamber having internal pressure which opposes said restorative biasing force;
   e. a secondary chamber, said secondary chamber having an internal pressure which exerts a force on said valve that is in substantially the same direction as said restorative biasing force;
   f. a equalization conduit, said equalization conduit providing fluid communication between said primary chamber and said secondary chamber; and
   g. an ambient actuation conduit, said ambient actuation conduit providing fluid communication between said secondary chamber and the ambient environment.

2. A device for providing ventilatory support as in claim 1, wherein said biasing member comprises a spring.

3. A device for providing ventilatory support as in claim 1, wherein said valve comprises a piston.

4. A device for providing ventilatory support as in claim 1, wherein said valve comprises a diaphragm.

5. A device for providing ventilatory support as in claim 1, wherein said inlet chamber is in fluid communication with a source of compressed gas.

6. A device for providing ventilatory support as in claim 1, wherein said inlet chamber is in fluid communication with a patient connection port.

7. a device for providing ventilatory support of a patient, comprising:
   a. a patient connection port;
   b. a source of gas;
   c. a valve, said valve opening and closing as a result of pressure at said patient connection port, said valve opening at a pressure greater than pressure required for said valve to close;
   d. said source of gas providing flow to said patient connection port when said valve is closed;
   e. a primary chamber, said primary chamber receiving flow from said gas source when said valve is open, resulting force of internal pressure of said primary chamber directed onto said valve in the open direction;
   f. a secondary chamber, said secondary chamber having an internal pressure which exerts a force on said valve that is in opposition of internal force of said primary chamber;
   g. a equalization conduit, said equalization conduit providing fluid communication between said primary chamber and said secondary chamber; and
   h. an ambient actuation conduit, said ambient actuation conduit providing fluid communication between said secondary chamber and the ambient environment.

8. A device for providing ventilatory support as in claim 7, wherein said valve comprises a piston.

9. A device for providing ventilatory support as in claim 7, wherein said valve comprises a diaphragm.

10. A device for providing ventilatory support as in claim 7, wherein said valve is acted upon by a biasing member providing a restorative force.

11. A device for providing ventilatory support of a patient, comprising:
   a. a inlet chamber in fluid communication with a patient port and a source of gas;
   b. a housing, said housing containing a valve;
   c. a primary chamber, said primary chamber contained in said housing and having a greater internal pressure when said valve is open than when said valve is closed;
   d. a secondary chamber, said secondary chamber contained in said housing;
   e. a ambient actuation conduit, said ambient actuation conduit providing fluid communication between said secondary chamber and the fluid space outside said housing;
   f. an exhalation port; said exhalation port providing fluid communication between said primary chamber and the fluid space outside said housing;
   g. wherein the internal pressure of said secondary chamber is less than the internal pressure of said primary chamber whenever said ambient actuation conduit is un-occluded.

12. A device for providing ventilatory support as in claim 11, wherein said valve comprises a piston.

13. A device for providing ventilatory support as in claim 11, wherein said valve comprises a diaphragm.

* * * * *